United States Patent [19]

Yancey

[11] 4,083,365
[45] Apr. 11, 1978

[54] DUAL INTEGRATOR EEG ANALYZER

[76] Inventor: Don Robert Yancey, Tsukasa Hts. 202, Seki-Machi 2-873, Nerima-ku, Tokyo 177, Japan

[21] Appl. No.: 694,582

[22] Filed: Jun. 10, 1976

[51] Int. Cl.² ............................................... A61B 5/04
[52] U.S. Cl. ............................................... 128/2.1 B
[58] Field of Search ..................................... 128/2.1 B

[56] References Cited

U.S. PATENT DOCUMENTS

| | | | |
|---|---|---|---|
| 3,087,487 | 4/1963 | Clynes | 128/2.1 B |
| 3,172,404 | 3/1965 | Copenhaver et al. | 128/2.1 B |
| 3,281,534 | 10/1966 | Dersch | 128/2.1 R |
| 3,421,498 | 1/1969 | Gans | 128/2.1 B |
| 3,548,812 | 12/1971 | Paine | 128/2.1 B |
| 3,780,724 | 12/1973 | John | 128/2.1 B |
| 3,893,450 | 7/1975 | Ertl | 128/2.1 B |

FOREIGN PATENT DOCUMENTS 1,050,021  2/1959  Germany ........................ 128/2.1 B

OTHER PUBLICATIONS

Davis, "IRE Transactions on Medical Electronics V. PGME-", Jul., 1958, pp. 29–34.
Emide et al., "Electroencephalography & Clinical Neurophysiology" vol. 37, No. 2, pp. 185–187, Aug. 1974.

Primary Examiner—William E. Kamm
Attorney, Agent, or Firm—Schuyler, Birch, Swindler, McKie & Beckett

[57] ABSTRACT

An electroencephalograph (EEG) is connected to record the brain wave response of a subject to periodic stimuli. An EEG analyzer comprising a dual integrator circuit separately records positive and negative wave responses to the stimuli during predetermined intervals and combines the recorded responses in a composite analysis of the subject's response to the periodic stimuli.

8 Claims, 7 Drawing Figures

DUAL INTEGRATOR EEG ANALYZER

BACKGROUND OF THE INVENTION

1. Field of the Invention

This invention relates to an analyzer for EEG wave forms produced by periodic stimuli, and more particularly, to such an analyzer for use in perimeter measurements of a field of vision.

2. Description of the Prior Art

It has previously been known to measure the degree of EEG response from a subject to periodic visual stimuli and then to compute and record an average wave form from the measured response, as disclosed in U.S. Pat. No. 3,574,450. Analysis of the recorded responses by a human observer is necessary in such a system.

It has also previously been known to determine the effect an anesthetic on a subject by measuring the EEG response to periodic electrical shocks, as described in U.S. Pat. No. 3,513,834. In such a system, integrators and time-delayed gates have been used to sum the responses occurring in certain windows of time following the simulus. However, no provision has been in such prior systems for distinguishing between positive and negative excursions to derive the information represented by that distinction.

Other U.S. Pat. Nos. 2,897,476 and 3,074,642, as well as an article by Sciarretta, et al. in Medical and Biological Engineering, Vol. 8, No. 5, pages 517–519, dated September 1970, disclose integrator arrangements which are somewhat similar to that used in an embodiment of the present invention, but which function in a different manner for a different purpose.

Ordinary analysis of brain waves is usually accomplished by a costly computer of averaged transients that retrieves a repetitively evoked brain wave from non-filterable random electrical noise. Because the noise is random, by repeated adding of the evoked brain wave, the signal-to-noise ratio can be improved by a factor $N^{\frac{1}{2}}$, where N is the number of times the transient (evoked brain wave) is averaged. Whether a signal is present or not can then be determined.

For certain stimuli, the shape of the brain wave is well known (see C. Ciganek, "The EEG Response (Evoked Potential) To Light Stimulus in Man", Electroenceph. lin. Neurophysiol., 1961, 165–172). Therefore, because there are two major negative waves between approximately 80–100 msec, 120–180 msec and one major positive evoked wave between approximately 180–240 msec, it is necessary to sample the evoked transient at one or more of these three intervals to determine whether there is a signal (positive or negative) above the expected level of noise.

Briefly, because noise is random, sometimes negative and sometimes positive, the noise tends to cancel itself out over a period of time. On the other hand, the evoked brain wave signal can be added up over the same period of time.

SUMMARY OF THE INVENTION

The principle of this perimeter, which is a device used to measure visual field for the purpose of detecting and diagnosing eye disorders, is that flashing points of lights, when perceived by the subject, will evoke brain waves which can be detected by special electronic circuits. The perimeters which are presently in wide use require much time to use and great subject cooperation and physician skill. The subject responds orally as to whether or not he thinks he can see the test target. Test results are highly subjective and are not accurate. The cost of perimeters is usually quite high and the more sophisticated perimeters are bulky. In contrast to the presently available perimeters which result in error prone "subjective" tests, the perimeter disclosed herein uses brain wave analysis which results in much more "objective" tests. Also, a perimeter according to the invention can be accurate, compact and automatic, thus not requiring costly, scarce technicians. Alternatively, the present invention can be used to test for hearing ability by substituting audio tones of differing frequencies for light stimuli.

This automatic perimeter comprises a hemispheric bowl in which stationary target lights can be flashed on and off, a central fixation cross, an eye position sensor to determine when the eye is fixating, an audio tone to inform the subject when he is not fixating properly, and a motor to control the flashing on and off of the target lights and to control the evoked brain wave analyzer and recorder.

The subject sits with his eye at approximately the center of a hemisperhic bowl. The bowl includes the central fixation cross toward which the subject is encouraged to focus. The bowl also includes a plurality of positions for the stationary flashing target lights, only one of which is operated at a time to provide a test of a corresponding part of the visual field. An eye-position sensor and an automatic control unit determine when the eye is directed at the fixation cross. The automatic control unit signals when the eye is directed away from the cross and the testing procedure is stopped. A timer/sequencer unit selects and flashes a first target light or stimuli in the bowl which evokes a response from the subject as indicated by the resulting EEG waves. The timer/sequencer unit operates an electronic switch which functions to permit only those portions of the EEG wave within certain relevant time intervals to pass through to an EEG analyzer. The EEG analyzer distinguishes between the positive and negative wave segments and separately integrates both these wave segments over a first series of relevant time intervals during which substantially identical visual stimuli are provided. The two resulting integrated waves then are added together. At the end of the first series of identical stimuli, the sum is indicated by a meter and a record is made for the first selected stimuli or target. The system, when automatic, proceeds to measure values for other stimuli or targets in sequence. The system can also be operated by manual selection of targets.

DESCRIPTION OF THE PREFERRED EMBODIMENT

Figure 1:
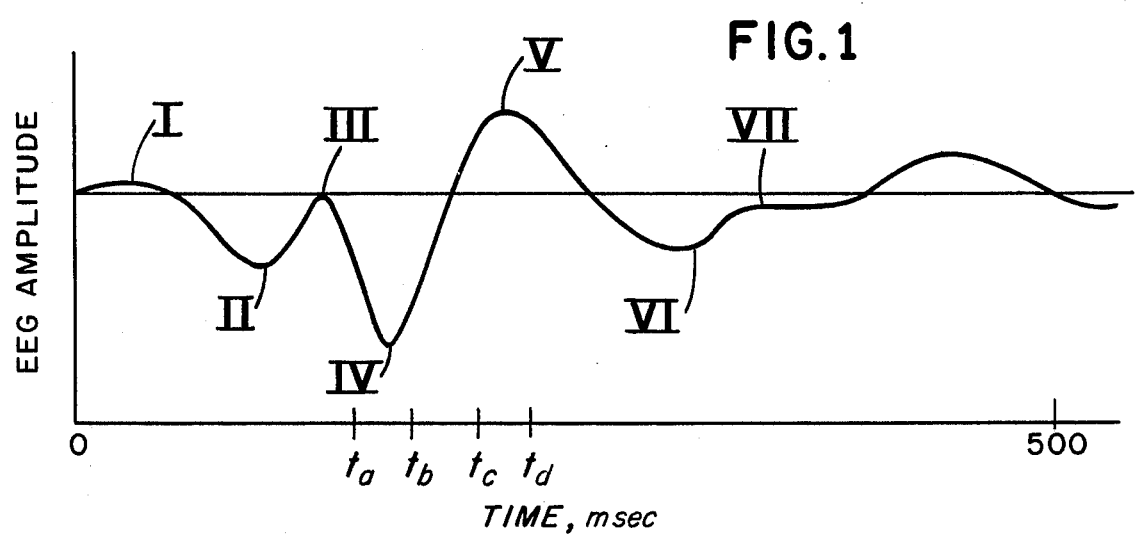
FIG. 1 is a chart of a typical EEG response wave during the first 500 msec following a visual stimulus.

The brain wave analyzer of the preferred embodiment samples one or more time intervals during which a response to the stimuli as indicated by the brain wave analyzer is likely to occur. The resulting signal from the sampled interval is fed into two separate half-wave rectifiers. One rectifier rectifies positive-going signals; the other rectifies negative-going signals. The outputs from the two half-wave rectifiers then are added together by an algebraic adder.

After a series of N resulting signals from the same sampled time interval have been processed through the half-wave rectifiers and the algebraic adder, a voltage indicative of the summed value of the evoked waves is obtained. If this voltage is significantly greater than expected for noise alone, a response to the stimuli can confidently be assumed to have been evoked. The level of confidence can be increased by increasing N, raising the level of the final output voltage required in order to be considered significantly greater than the noise level, and by adding additional integrators for sampling of other time intervals corresponding to the two remaining principal evoked wave segments. The existence of a significant summed value after the stimulus (such as a flashing light for a perimeter, reversing a checkerboard for visual acuity, or audible tones for hearing ability tests) is applied N times indicates that the stimulus has been perceived by the subject. If no evoked signal is found to exist after N applications of the stimulus, the apparatus proceeds to the next stimulus.

In a preferred embodiment of this invention for use as a perimeter, the source of the stimuli is approximately 85 small lights arranged around intersecting vertical and horizontal axes.

For the apparatus to apply the stimuli, the subject must be fixating on the central fixation cross at the intersection of the two axes. The fixation cross is a luminous red cross. The eye tracker determines whether the eye is properly fixated. When the eye is not fixated, a signal disappears from the output of the eye-tracker, the subject hears an audible tone, the apparatus discontinues application of the stimulus, and analysis is stopped until the eye is again properly fixated.

The eye-position sensor helps to assure proper fixation by taking advantage of three facts: (1) infra-red light (IR) is invisible to the human eye; (2) IR is reflected by the cornea and various other surfaces of the eye; (3) the visual field of the normal human eye is approximately 110° temporal, 60° nasal. Proper fixation is extremely important to assure accurate test results.

Because IR is invisible, photophobia is avoided, and a small IR source can be directed and focused on the cornea by means of a beam splitter intersecting the space between the eye and the fixation cross. The instrumentation for the eye-tracker is positioned on the nasal side of the eye out of the visual field. By means of the same beam splitter, the returning IR reflection can be directed back into the eye-tracker and detected by an IR photodetector.

When the eye is looking straight ahead and fixating on the fixation cross, the IR beam is reflected back into the IR detector which produces an output that is used to allow automatic testing to proceed and to silence the audio tone which indicates non-fixation.

FIG. 1 shows the wave form of a typical visual-evoked response (VER) to a flashing light. The principal segments of a VER wave are labelled I to VII in the figure. To determine whether a VER wave form is present in an EEG, segments II, IV, V and VI are most useful to analyze.

Figure 3:
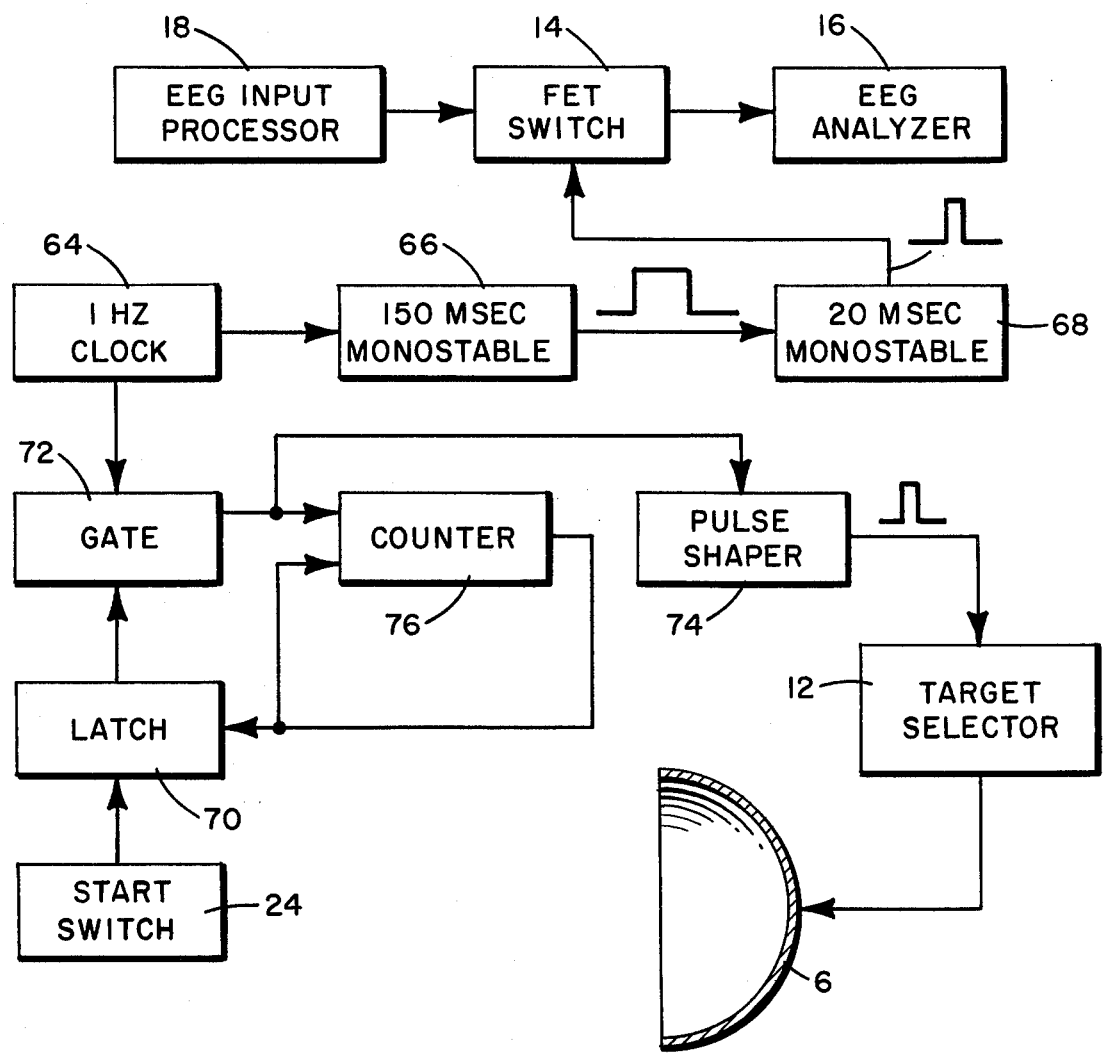
FIG. 3 is a block circuit diagram of a system using the present invention in which the system can be partially manually operated.
Figure 2:
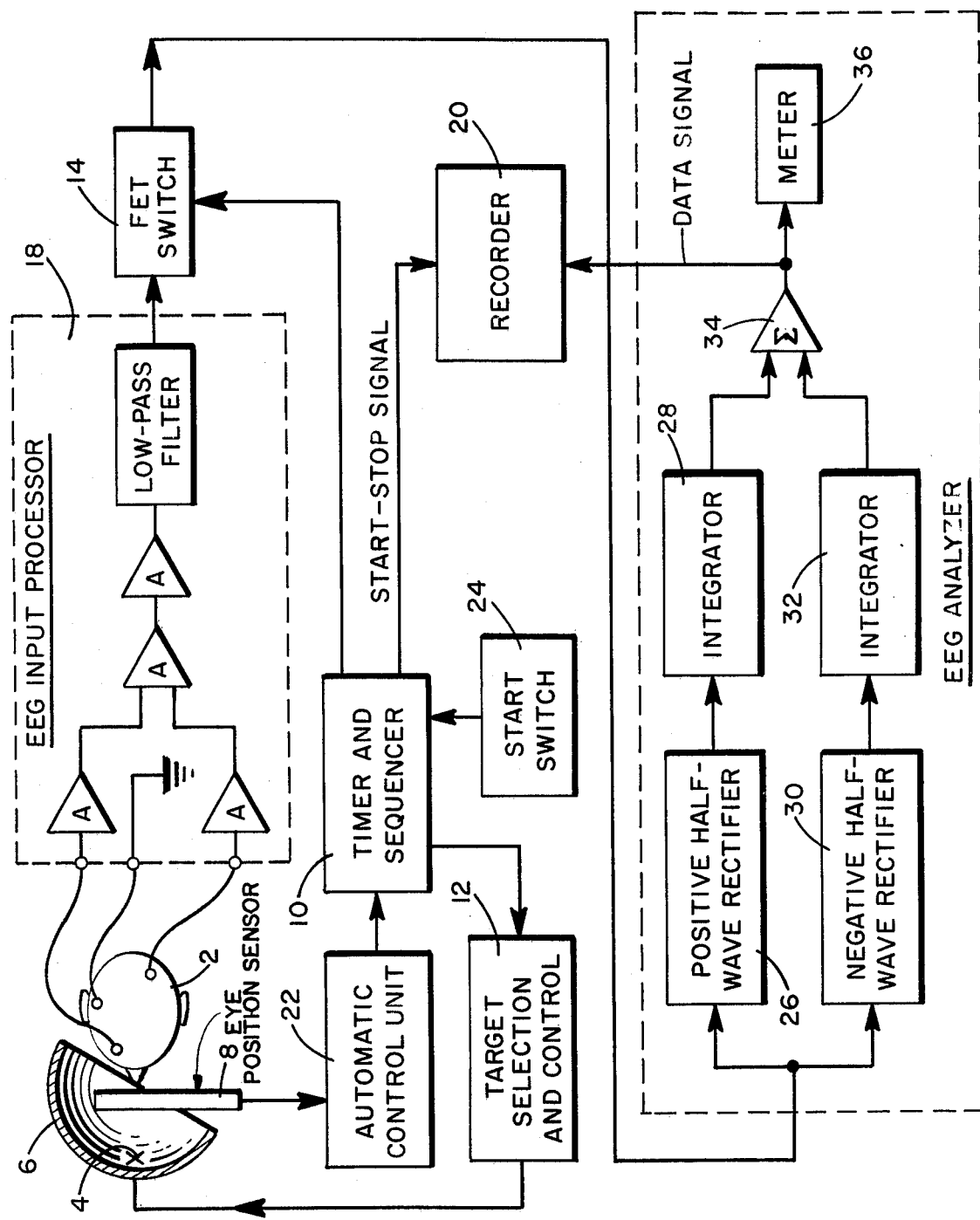
FIG. 2 is an overall block circuit diagram of an embodiment of the present invention in an automatic mode.

For example, the automatic objective perimeter circuit in FIGS. 2 and 3 can be utilized to examine the time interval $t_a - t_b$ to measure whether a negative wave is present; and/or interval $t_c - t_d$ to measure whether a positive wave is present.

FIG. 2 shows a block diagram of an automatic objective perimeter. The patient 2 looks at a fixation cross 4 while lights are flashed at selected locations on the hemisphere bowl 6. Eye position sensor 8 helps assure that the patient continues to fixate throughout the perimeter examination.

The timer and sequencer unit 10 generates an initial timing pulse and additional pulses at one-second intervals thereafter. These timing pulses trigger the target selector/stimulus circuit 12 which selects the locations of the flashing lights or targets in the hemispheric bowl 6 and causes these targets to flash briefly at one-second intervals. These timing pulses also activate FET switch 14 which passes the VER signal at appropriate time intervals, for example, between $t_a$ and $t_b$ or $t_c$ and $t_d$, to the EEG analyzer circuit 16.

Each time a flashing target is perceived by the patient, a VER is generated which is amplified by EEG input processor 18. If no VER is generated, this indicates a scotoma (blind spot) for a corresponding location in the retina.

At the end of a number N of target flashes from one target location, the EEG analyzer 16 determines whether one of the principal segments of the VER wave is present, for example, the IV wave of FIG. 1. A "YES" output is generated by the EEG analyzer 16 if the voltage level of the output is above some predetermined level. The EEG analyzer 16 then causes the recorder 20 to mark an appropriate "YES" response for the corresponding location on the recorder chart paper. If, on the other hand, the generated voltage level of the output is below some predetermined level, indicating a "NO" response, then nothing is recorded by recorder 20.

It is also possible for the EEG analyzer 16 to generate outputs which are neither "YES" nor "NO" (between two predetermined levels) depending on the degree of the scotoma. That is, an intermediate output generated by the EEG analyzer 16 which indicates an intermediate scotoma. Appropriate recording techniques can be utilized to indicate this condition.

After a number N of target flashes from one target location, the target selection and control circuit 12 successively selects the next target locations. The results from each of these selected target locations are recorded by recorder 20 in the same manner as described above. Throughout this testing process, the automatic control unit 22 automatically controls the operation of the perimeter by sensing whether the eye is focusing on the fixation cross. A start switch 24 controls initial operation.

Within the EEG analyzer 16, rectifier 26 is a positive half-wave rectifier which supplies a signal to an integrator 28. Rectifier 30 is a negative half-wave rectifier which supplies a signal to an integrator 32.

If, for example, the automatic objective perimeter of FIG. 2 is set for interval $t_a - t_b$ and the VER is present, then negative wave segment IV will be rectified by rectifier 30 and integrated by integrator 32. The output voltage from integrator 28 will be zero, or only nominally positive, and therefore the output from adder 34 to meter 36 and recorder 20 will be negative, indicating the presence of the VER.

If the VER is not present, the waves appearing in interval $t_a - t_b$ will tend to be randomly positive and negative. Therefore, after N number of analyses, the outputs from integrators 28 and 32 will be approximately equal. The output of the adder 34 will be approximately zero, indicating no VER.

Figure 4:
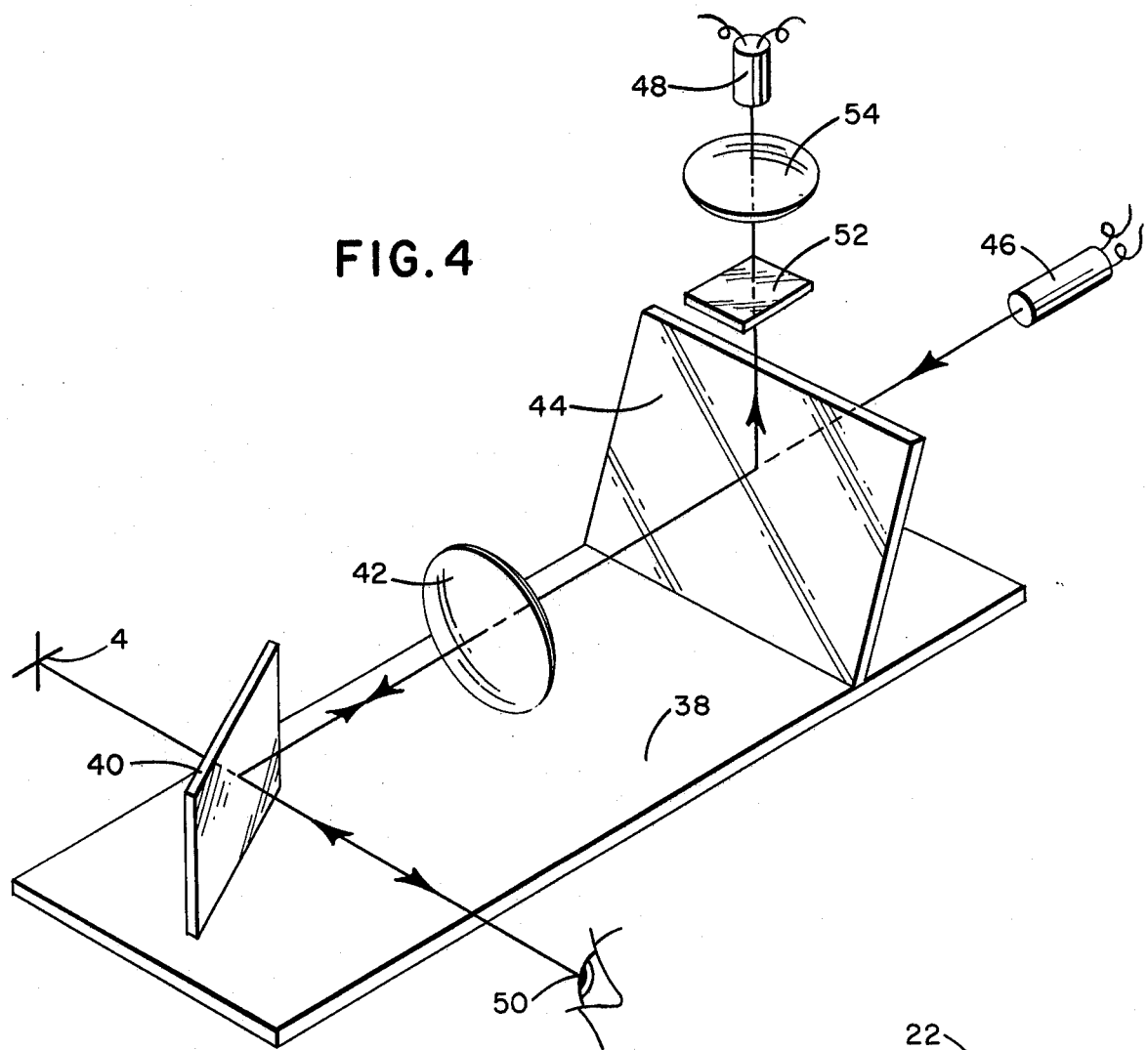
FIG. 4 is a perspective view of an optical system used in an eye position sensor in the system of FIG. 2.

FIG. 4 shows a perspective view of the eye position sensor 8, including a mounting plate 38, infrared (IR) reflecting mirror 40, focusing lens 42, IR beam splitter 44, IR emitter 46, IR detector 48, eye cornea 50 and fixation cross 4. If the eye is properly fixating on cross 4, the IR light from source 46 is reflected by the eye cornea 50 into IR detector 48. The path of the incident and reflected IR light is indicated by lines and arrows in FIG. 4. If the eye does not properly fixate, the reflection from the cornea will not be detected by IR detector 48. IR filter 52 ensures detecting of IR reflected from the cornea only, and a lens 54 focuses reflected IR on detector 48.

Figure 5:
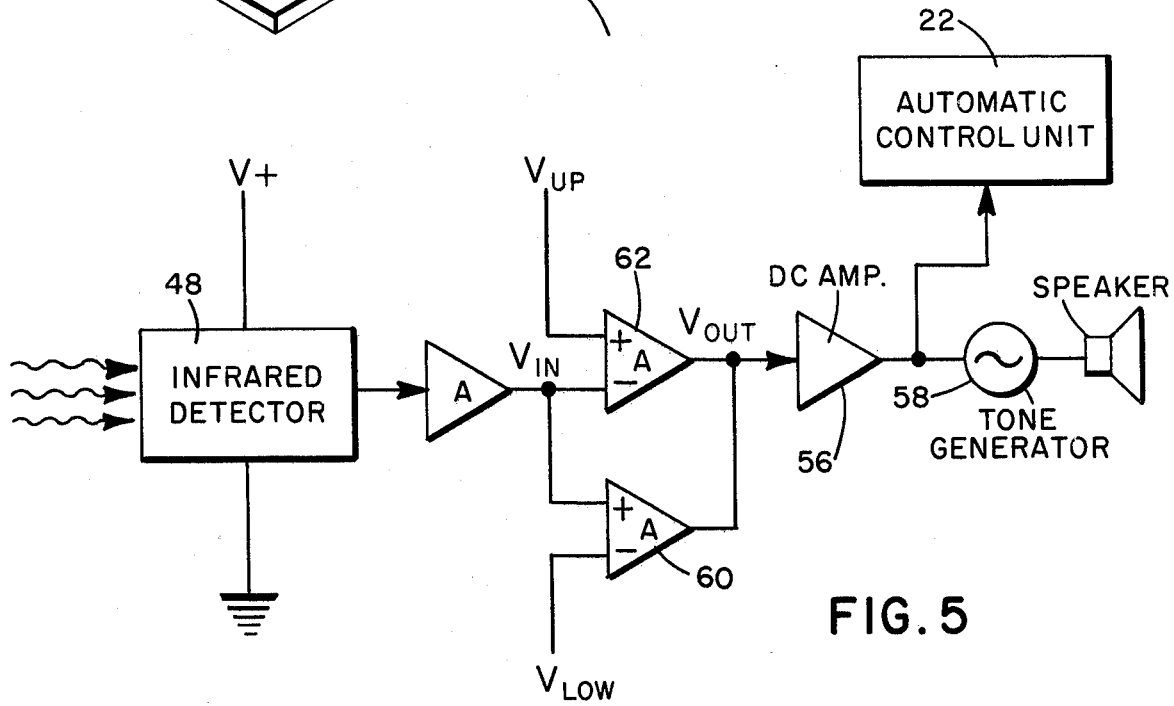
FIG. 5 is a block circuit diagram of an electrical circuit used with the eye position sensor.

FIG. 5 shows the circuit of the eye position sensor 8. When the eye is properly fixating, the input voltage $V_{IN}$ will be between reference or threshold voltages $V_{UP}$ and $V_{LOW}$. The corresponding output voltage $V_{OUT}$ will then be zero. As a result, the output from the DC amplifier 56 will also be zero. Thus, the tone generator 58 will not produce an audible tone.

If $V_{IN}$ is either less than $V_{LOW}$, or greater than $V_{UP}$, the differential comparators 60 and 62, respectively, will generate an output voltage $V_{OUT}$ which will trigger the tone generator 58. An audible tone will be produced and the automatic control unit 22 will cause the perimeter examination to stop until the patient again properly fixates.

The operation of the eye position sensor 8 can be summarized as follows:

if $V_{IN} > V_{UP}$, then $V_{OUT}$ occurs, tone is heard, examination discontinues;

if $V_{IN} > V_{LOW}$, then $V_{OUT}$ occurs, tone is heard, examination discontinues;

if $V_{UP} > V_{IN} > V_{LOW}$, then no $V_{OUT}$ occurs, no tone is heard, the examination continues.

A more detailed description of the eye position sensor in FIG. 5 is found in my co-pending application entitled EYE POSITION SENSOR, Ser. No. 695,131, which was filed on June 11, 1976.

FIG. 3 is a more detailed block circuit diagram of portions of a device similar to that of FIG. 2, including features which allow it to be operated partially manually. A one hertz clock 64 drives two successive monostable elements 66 and 68 to provide a timing signal which is used to gate the EEG signal through gate 14. When start switch 24 is operated, it sets latch 70 to open gate 72 to pass the clock signals to a pulse shaper 74. Pulses from pulse shaper 74 pass through the target selector 12 to the flashing targets in bowl 6. A counter 76 counts the number of repetitions of one target before the latch 70 is reset to close gate 72. At this point, the target selector 12 can be changed manually and the start button pushed again.

As a further alternative, large numbers of (i.e., more than two) integrators may be used, each integrator having its input limited to a positive or negative value. The various integrators could be respective to the different segments of the VER wave of FIG. 1 by gating the integrators with appropriate time delay circuits. Thus, more than one segment of the VER wave could be factored into the weighting function to determine whether the subject is responding to the applied stimuli. The integrator outputs could be applied in parallel to an adder, summer or AND circuit to derive a combined value.

Figure 6:
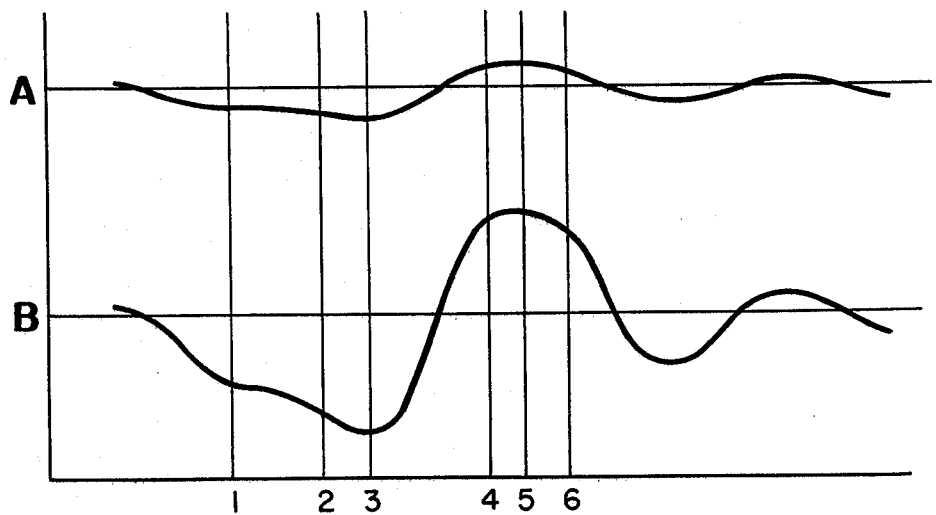
FIG. 6 is a chart of a relatively weak evoked response and of a relatively strong evoked response which are each sampled at multiple points.
Figure 7:
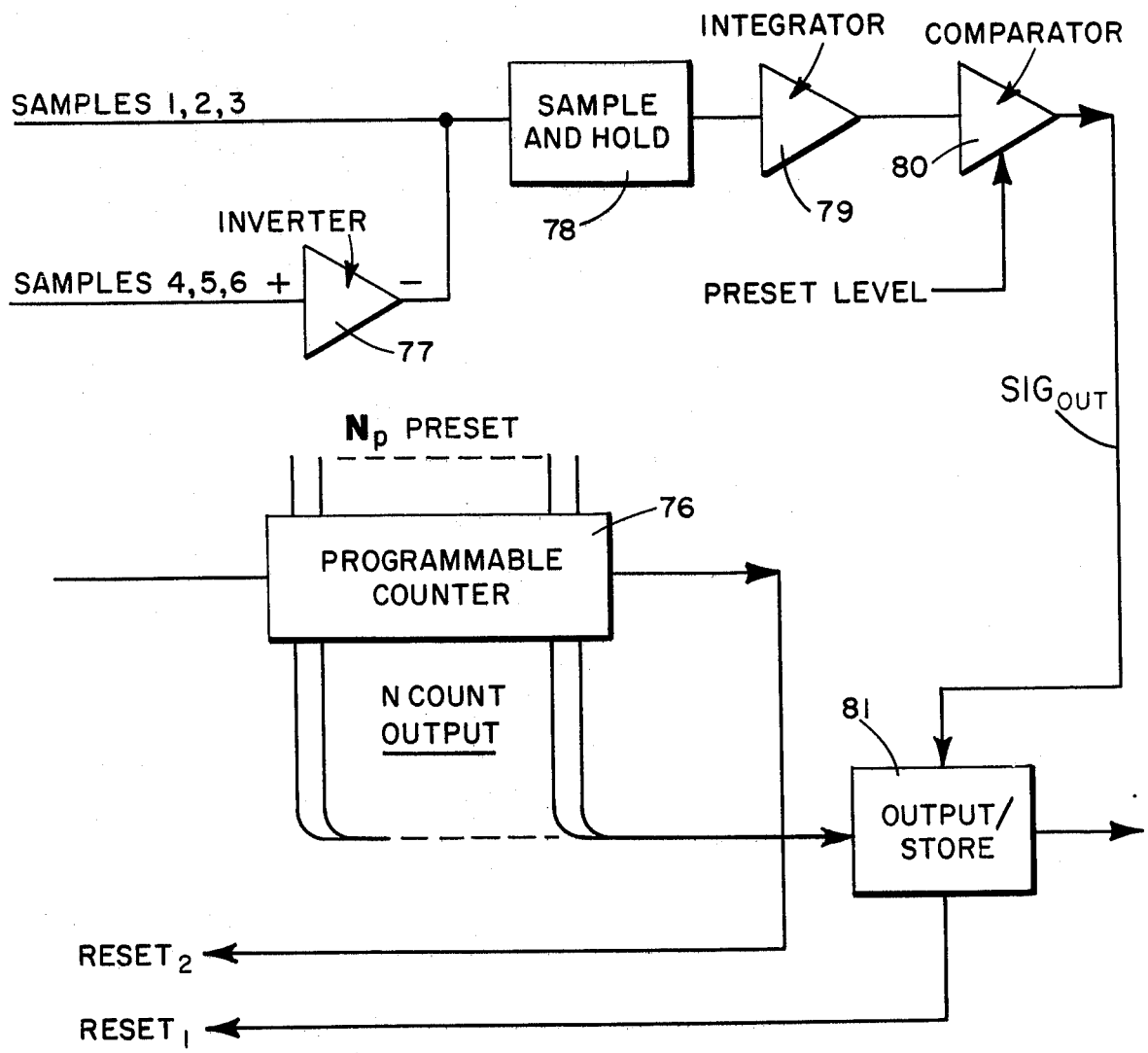
FIG. 7 is a block diagram of the electrical circuit which is used to obtain a digital output of the analyzed EEG.

FIG. 6 generally shows the same characteristic evoked response shown in FIG. 1. Waveform A gives a relatively weak response and waveform B is a relatively strong response. Both waveforms are shown with six sample points, three of which are negative and the other three of which are positive. FIG. 7 shows an electrical circuit for providing a digital output representative of the EEG signal shown in FIG. 6. The inverter 77 changes the polarity of samples 4, 5 and 6 to correspond to the polarity of samples 1, 2, and 3. The sample and hold circuit 78 and the integrator 79 add up the evoked response. At the same time, the programmable counter 76 is providing a digital count N to the output store 81. When the preset level of comparator 80 is reached, a signal SIG OUT is provided by comparator 80 to output store 81 to cause output store 81 to supply the digital count N at its output. This digital count N represents the number of repeated stimuli necessary for the comparator 80 to supply the signals SIG OUT to the output store 81 after evaluating samples 1 to 6 (or 1 to A, where A is the number of samples per evoked response). The output store 81 also produces reset signal 1 for resetting the circuit after receiving the signal SIG OUT from the comparator 80. However, if the preset level of the comparator 80 is not reached by the count of Np of programmable counter 76, then reset signal 2 is automatically produced by programmable counter 76 for resetting the circuit.

Another alternative embodiment envisions use of backward extrapolation to determine the response threshold by determining the number of applications of stimuli to a given part of the visual field which are necessary for the output of the EEG analyzer to reach a predetermined value.

Although the present invention has been illustrated in terms of the preferred embodiment, it will be obvious to one of ordinary skill in the art that numerous modifications may be made without departing from the true spirit and scope of the invention and therefore the scope of the invention is to be limited only by the appended claims.

What is claimed is:

1. A device for analyzing the EEG signal of a subject in response to periodic stimuli; the improved means for analyzing the EEG signal comprising:
   (A) a timer and switch means for passing the EEG signal only during at least one time interval of preset duration beginning a predetermined time after each of a plurality of periodic stimuli, thereby obtaining a gated EEG signal,
   (B) rectifier means for dividing the gated EEG signal into positive-going signals and negative-going signals,
   (C) first integrator means for integrating the positive-going signals, (D) second integrator means for integrating the negative-going signals, and (E) means for algebraically combining output signals from the first and second integrator means for measuring the degree of response of the subject to the periodic stimuli.

2. A device according to claim 1 wherein said device is used to analyze the perimeter measurements of a field of vision, said device further comprising:

(A) means for flashing a target light at periodic intervals in a selectively adjustable location within the subject's visual field, (B) means for recording the degree of response of the subject to the visual periodic stimuli as a function of the location of the flashing target light, and (C) means for adjusting the location of the flashing target light after a predetermined time, whereby the degree of response of the subject to the flashing target light can be recorded for the subject's entire visual field.

3. A device according to claim 2, further comprising means for automatically controlling the operation of said device in response to the position of the subject's eye, wherein the operation of said device will be discontinued when the subject's eye is not directed at a predetermined fixation point.

4. A device according to claim 2 wherein said means for adjusting the location of the flashing target light after a predetermined time is automatic.

5. A device according to claim 2 wherein said means for adjusting the location of the flashing target light after a predetermined time is manual.

6. A device for measuring the perimeter of a field of vision by analyzing the EEG signal of a subject in response to periodic visual stimuli, the improved means for measuring the field of vision comprising:

(A) a timer and switch means for passing the EEG signal only during at least one time interval of preset duration beginning a predetermined time after each of a plurality of periodic visual stimuli, thereby obtaining a gated EEG signal, wherein said time interval is selected on the basis of the likelihood of a visually evoked response (VER), (B) means for analyzing the gated EEG signal including first and second means for separately evaluating positive and negative EEG signals, respectively, (C) recording means for measuring the degree of response of the subject of the visual periodic stimuli.

7. A device according to claim 6 wherein said analyzing means further comprises:

(A) rectifier means for dividing the gated EEG signal into positive-going signals and negative-going signals, (B) first integrator means for integrating the positive-going signals, (C) second integrator means for integrating the negative-going signals, (D) means for algebraically combining output signals from the first and second integrator for means.

8. A device according to claim 6, further comprising means for automatically controlling the operation of said device in response to the position of the subject's eye, wherein the operation of said device will be discontinued when the subject's eye is not directed at a predetermined fixation point.

* * * * *